(12) United States Patent
Hori et al.

(10) Patent No.: US 11,291,105 B2
(45) Date of Patent: Mar. 29, 2022

(54) PARTICLE BEAM ACCELERATOR AND PARTICLE THERAPY SYSTEM

(71) Applicant: HITACHI, LTD., Tokyo (JP)

(72) Inventors: Chishin Hori, Tokyo (JP); Takayoshi Seki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 17/042,398

(22) PCT Filed: Feb. 13, 2019

(86) PCT No.: PCT/JP2019/005150
§ 371 (c)(1),
(2) Date: Sep. 28, 2020

(87) PCT Pub. No.: WO2019/220714
PCT Pub. Date: Nov. 21, 2019

(65) Prior Publication Data
US 2021/0144839 A1 May 13, 2021

(30) Foreign Application Priority Data
May 16, 2018 (JP) .............................. JP2018-094277

(51) Int. Cl.
*H05H 13/02* (2006.01)
*A61N 5/10* (2006.01)
*H05H 7/04* (2006.01)

(52) U.S. Cl.
CPC ........... *H05H 13/02* (2013.01); *A61N 5/1078* (2013.01); *H05H 7/04* (2013.01); *A61N 2005/1087* (2013.01)

(58) Field of Classification Search
CPC ........ H05H 13/02; H05H 7/04; H05H 13/005; A61N 5/1078; A61N 2005/1087; A61N 5/1077
See application file for complete search history.

(56) References Cited

U.S. PATENT DOCUMENTS

| 4,139,777 A * | 2/1979 | Rautenbach | H05H 13/08 376/112 |
| 4,577,156 A * | 3/1986 | Kerst | H05H 11/00 315/504 |

(Continued)

FOREIGN PATENT DOCUMENTS

| JP | 2016-213198 A | 12/2016 | |
| JP | 2019133745 A * | 8/2019 | ............... A61N 5/10 |

(Continued)

OTHER PUBLICATIONS

International Search Report of PCT/JP2019/005150 dated Apr. 9, 2019.

*Primary Examiner* — David A Vanore
(74) *Attorney, Agent, or Firm* — Mattingly & Malur, PC

(57) ABSTRACT

In a magnetic device 1, on faces opposite to a middle plane 2 between an upper magnetic pole 8 and a lower magnetic pole 9, recesses 21a, 21b, 21c, and 21d and projections 22a, 22b, 22c, and 22d are alternately placed along a beam circling direction. In the projections 22a, 22b, 22c, and 22d, angle widths θ of the projections 22a, 22b, 22c, and 22d when viewed from the center O1 of a beam closed orbit is narrowed as beam energy is increased. On the outer circumferential region of the recess 21a on the upper magnetic pole 8 and the lower magnetic pole 9, the inlet of an extraction channel 1019 that extracts a beam accelerated to a predetermined energy to outside an accelerator 1004 is provided.

7 Claims, 12 Drawing Sheets

(56) References Cited

U.S. PATENT DOCUMENTS

| | | | | |
|---|---|---|---|---|
| 4,641,104 | A * | 2/1987 | Blosser | H05H 7/20 |
| | | | | 250/493.1 |
| 7,656,258 | B1 * | 2/2010 | Antaya | H05H 13/02 |
| | | | | 335/216 |
| 2009/0315424 | A1 * | 12/2009 | Vollmer | H02K 1/278 |
| | | | | 310/156.43 |
| 2011/0291484 | A1 * | 12/2011 | Tsutsui | H05H 13/00 |
| | | | | 307/66 |
| 2012/0273164 | A1 * | 11/2012 | Vetrovec | H01L 31/0521 |
| | | | | 165/104.13 |
| 2014/0094637 | A1 | 4/2014 | Zwart et al. | |
| 2015/0084548 | A1 * | 3/2015 | Hara | H05H 13/005 |
| | | | | 315/501 |
| 2015/0231411 | A1 * | 8/2015 | O'Neal, III | A61N 5/1043 |
| | | | | 600/1 |
| 2017/0303384 | A1 * | 10/2017 | Aoki | H05H 13/005 |
| 2017/0318657 | A1 * | 11/2017 | Aoki | H05H 7/08 |
| 2017/0332474 | A1 * | 11/2017 | Abs | H05H 7/10 |
| 2017/0339778 | A1 * | 11/2017 | Aoki | H05H 13/10 |
| 2019/0232085 | A1 * | 8/2019 | Hori | H05H 13/005 |
| 2019/0239333 | A1 * | 8/2019 | Aoki | H05H 7/08 |
| 2019/0239334 | A1 * | 8/2019 | Aoki | H01F 7/202 |

FOREIGN PATENT DOCUMENTS

| | | | | |
|---|---|---|---|---|
| JP | 2019200899 A | * | 11/2019 | A61N 5/1077 |
| JP | 2020038797 A | * | 3/2020 | A61N 5/10 |

* cited by examiner

PARTICLE BEAM ACCELERATOR AND PARTICLE THERAPY SYSTEM

TECHNICAL FIELD

The present invention relates to a particle beam accelerator and a particle therapy system equipped with the same.

BACKGROUND ART

As an example of synchrocyclotron particle accelerators using magnetic field flutter, Patent Literature 1 describes a particle accelerator including a voltage source to sweep a radiofrequency voltage in a cavity to accelerate particles from a plasma column, the voltage source being the plasma column, a magnet to cause particles to move orbitally within the cavity, a regenerator, and ferromagnetic arrangements located in the cavity with a space from the regenerator, the ferromagnetic arrangements being configured to cancel a magnetic field bump formed by a magnet.

CITATION LIST

Patent Literature

Patent Literature 1: Japanese Patent Application Laid-Open No. 2016-213198

SUMMARY OF INVENTION

Technical Problem

Nowadays, a reduction in the size of a particle therapy system used for radiotherapy is advancing. Patent Literature 1 discloses the magnetic pole shape of a magnetic device that produces a magnetic field necessary for a synchrocyclotron specifically, on a particle beam accelerator referred to as a synchrocyclotron included in a small-sized particle therapy system.

Generally, a particle beam accelerator referred to as a circular accelerator includes an injection device including an ion source, a magnetic device that produces a primary magnetic field for causing a beam to stably circle, an acceleration cavity that feeds a radiofrequency electric field to accelerate the beam, a beam displacement producing magnet that feeds a magnetic field for intentionally shifting the beam from an equilibrium orbit, and an extraction channel that extracts the beam displaced from the equilibrium orbit to outside the accelerator.

In order to accelerate a beam to a desired energy by the circular accelerator, it is necessary to match the timing, at which the beam passes the acceleration cavity, with the phase of a radiofrequency electric field.

A synchrocyclotron is a device that produces a static magnetic field using a magnetic device, modulates the frequency of a radiofrequency electric field matching the frequency with the energy of the beam to match the timing, at which the beam passes an acceleration gap, with the phase of the radiofrequency electric field, and accelerates the beam to desired energy.

Since in the synchrocyclotron, the beam is accelerated in the static magnetic field, the orbit drawn by the beam spreads as energy is higher. The beam accelerated to a predetermined energy by the accelerator senses the magnetic field fed by the beam displacement producing magnet, this causes the beam to be intentionally displaced from the equilibrium orbit, the beam reaches the extraction channel, and then the beam is extracted to outside the accelerator.

The extraction channel is often formed of a referred to as septum. A magnetic field in the opposite direction to the direction of the primary magnetic field using septum, and thus the orbit radius of the beam passing the extraction channel is increased. The beam whose orbit radius is increased using septum is left from the closed orbit, and guided to a beam transport system and an irradiation system in the subsequent stage.

Such a reduction in the size of the synchrocyclotron means an increase in the primary magnetic field. However, an increase in the primary magnetic field results in an increase in a magnetic field that has to be produced by septum for extracting a beam. Particularly, when the primary magnetic field becomes a high magnetic field of about three tesla or more, the primary magnetic field is produced using a superconducting coil.

Here, septum is typically formed of a resistive magnet from the restriction of the size of installation spaces and the characteristics of its operating method in which septum is used in a pulse form because septum is not temporally constant. In the resistive magnet, when a magnetic field of one tesla or more is desired to be produced, there are various difficulties, such as an increase in the size of septum, an increase in a power supply capacity, and an increase in the power consumption of cooling the coil.

Therefore, a reduction in the size of the accelerator is defined by the limitation of septum, not by primary magnetic field strength.

Therefore, a technical problem that the present invention is to solve is to provide a small-sized particle beam accelerator that extracts a beam more easily than a conventional one and a particle therapy system equipped with the same in a synchrocyclotron type particle beam accelerator including an acceleration cavity that can modulate frequencies.

Solution to Problem

Although the present invention includes several solutions to the problem, an example is a particle beam accelerator including an acceleration cavity that enables modulation of a frequency of radiofrequency electric field to accelerate a beam, and a magnetic device that produces a static magnetic field. The magnetic device has a return yoke and a pair of magnetic poles fixed to the return yoke. The pair of magnetic poles are placed at positions in surface symmetry with respect to a middle plane in a space sandwiched between the pair of magnetic poles. On a face opposite to the middle plane of the magnetic pole, a recess and a projection are alternately placed along a beam circling direction. In the projection, an angle width of the projection when viewed from a center of a beam closed orbit is narrowed as beam energy is increased. In a magnetic pole outer circumferential region of the recess, an inlet of an extraction channel from which a beam accelerated to a predetermined energy is extracted to outside the particle beam accelerator is provided.

Advantageous Effects of Invention

According to the present invention, a small-sized particle beam accelerator that easily extracts a beam can be provided. Problems, configurations, and effects other than ones described above will be apparent from the description of embodiments below.

DESCRIPTION OF EMBODIMENTS

In the following, embodiments of a particle beam accelerator and a particle therapy system according to the present invention will be described with reference to the drawings.

First Embodiment

A first embodiment of a particle beam accelerator and a particle therapy system according to the present invention will be described with reference to FIGS. 1 to 7.

Figure 1:
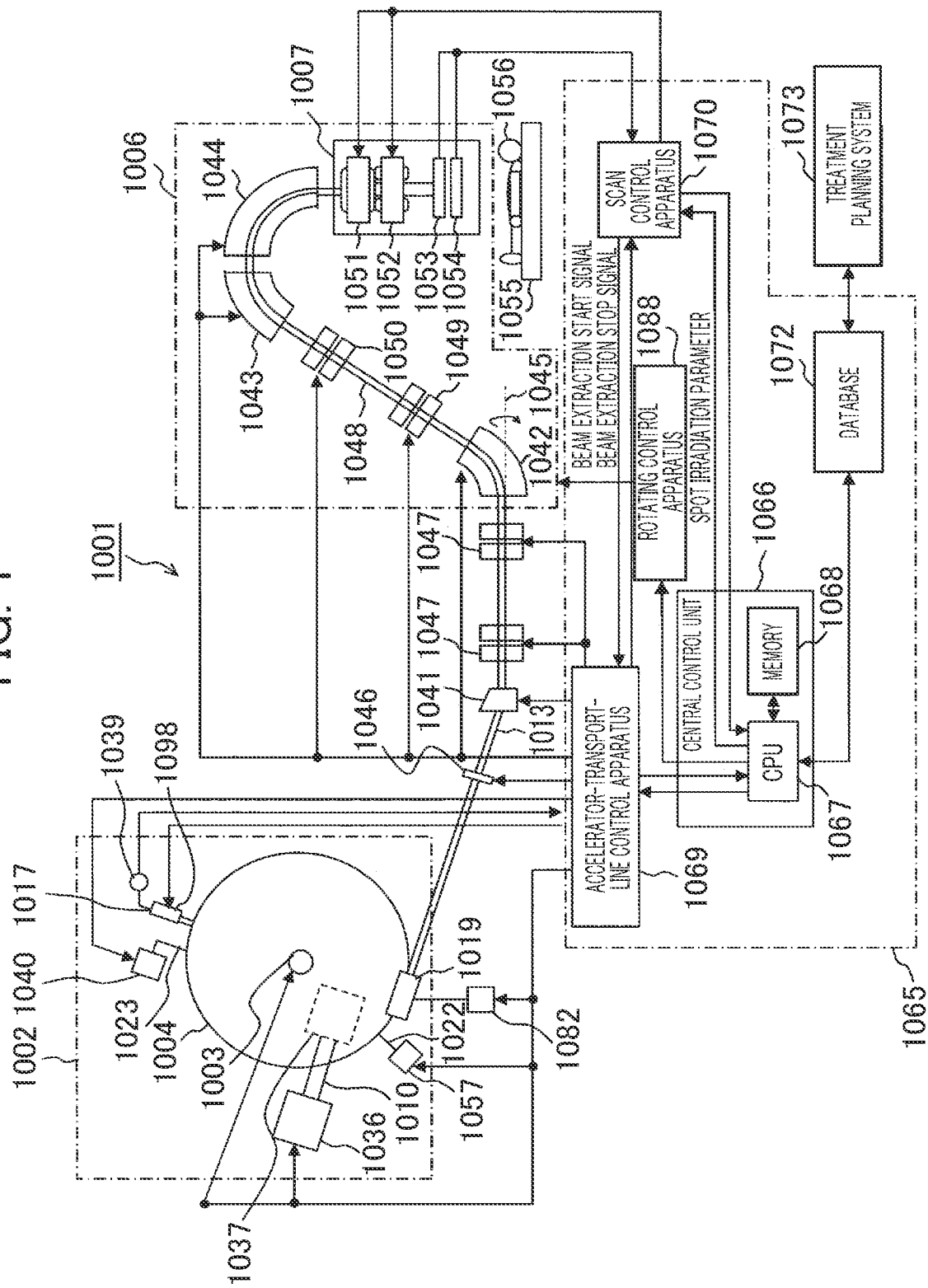
FIG. 1 is a block diagram of the particle therapy system according to a first embodiment of the present invention.
Figure 2:
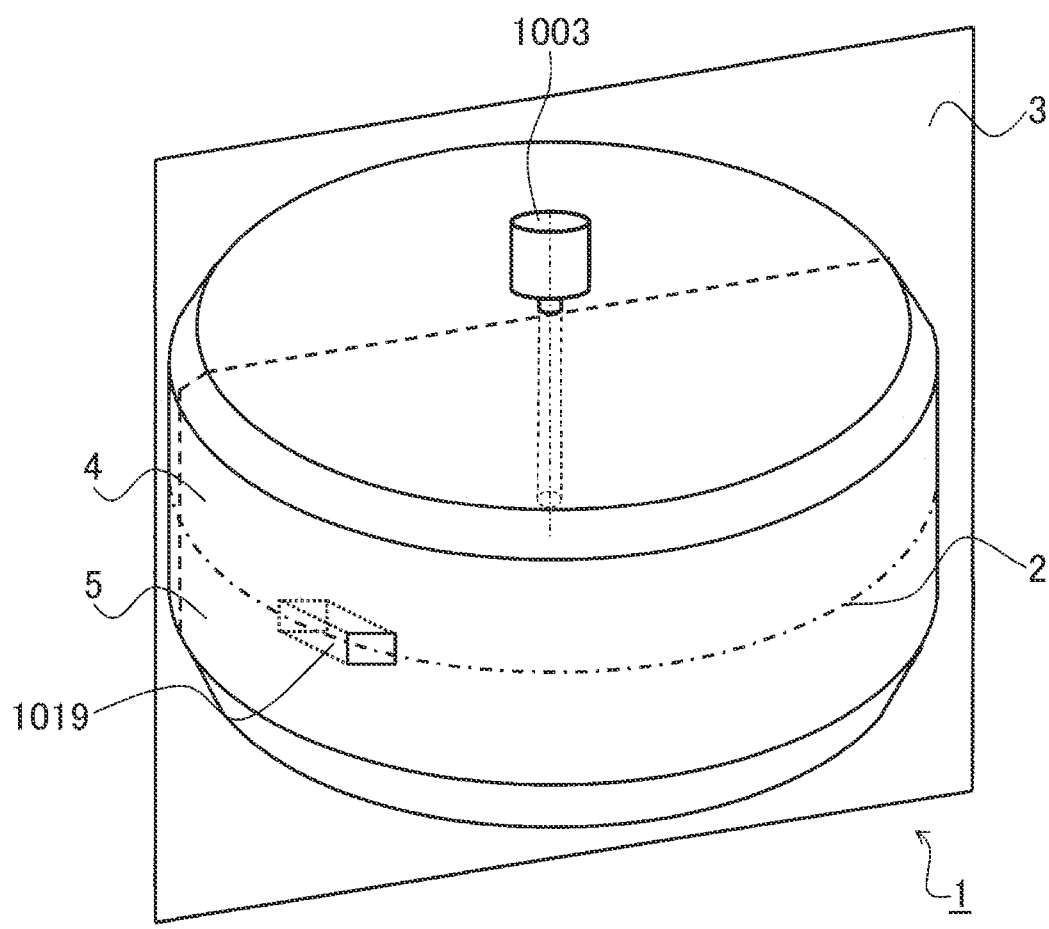
FIG. 2 is a perspective view of a magnetic device placed in an accelerator of the particle therapy system according to the first embodiment.
Figure 3:
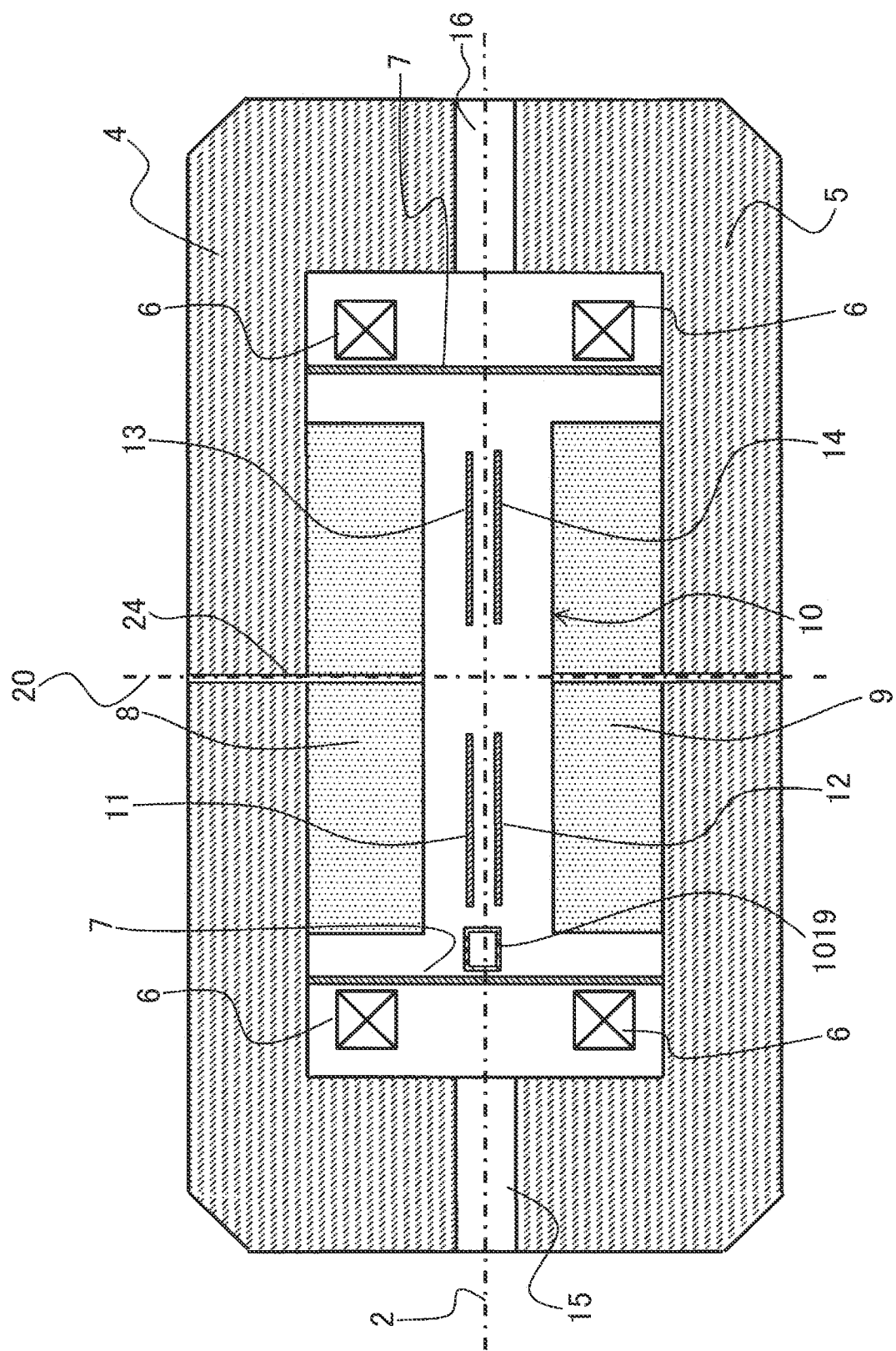
FIG. 3 is a cross sectional view of the magnetic device according to the first embodiment taken along a vertical plane.
Figure 4:
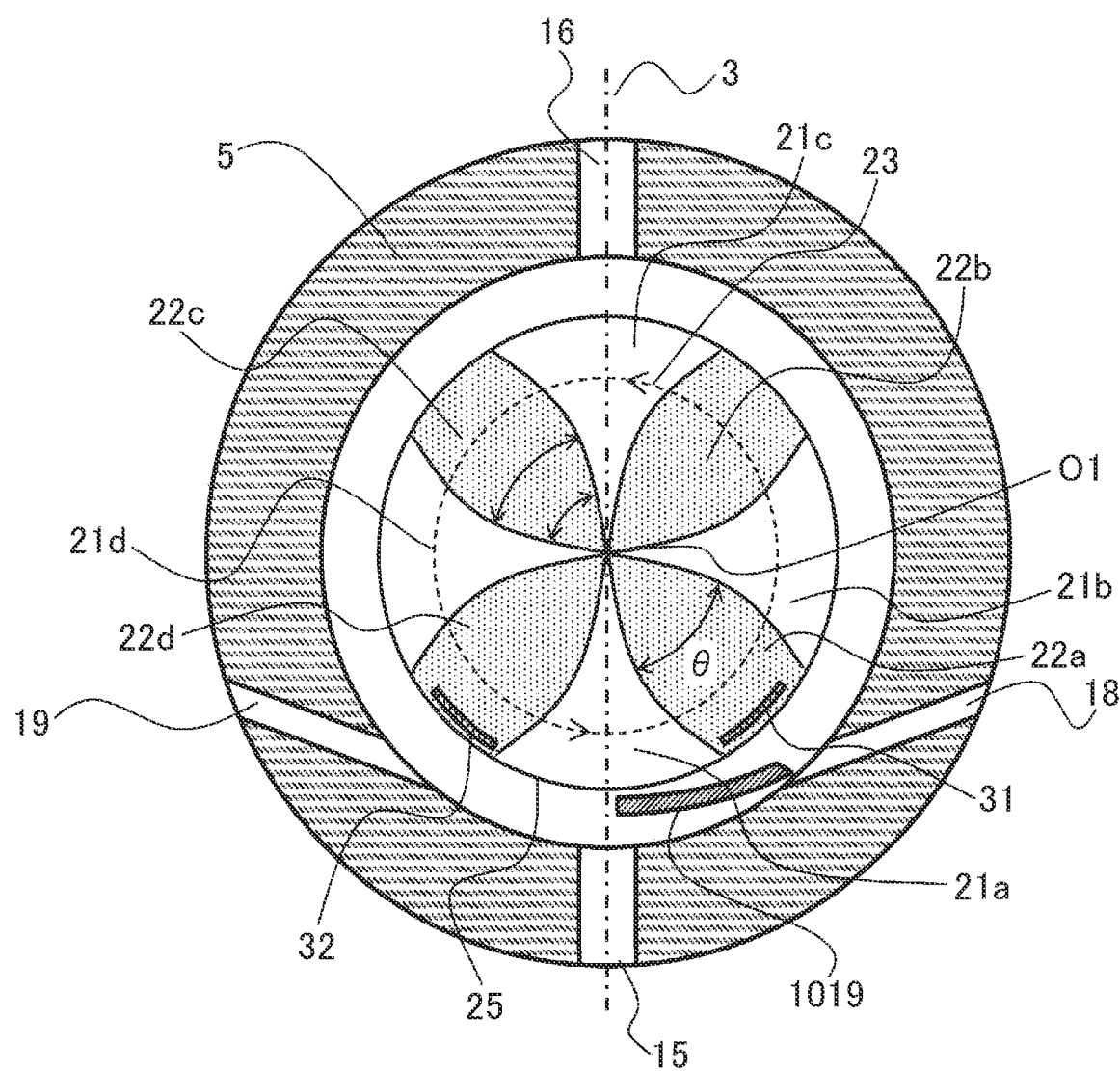
FIG. 4 is a plan view of the magnetic device according to the first embodiment viewed from a middle plane.
Figure 5:
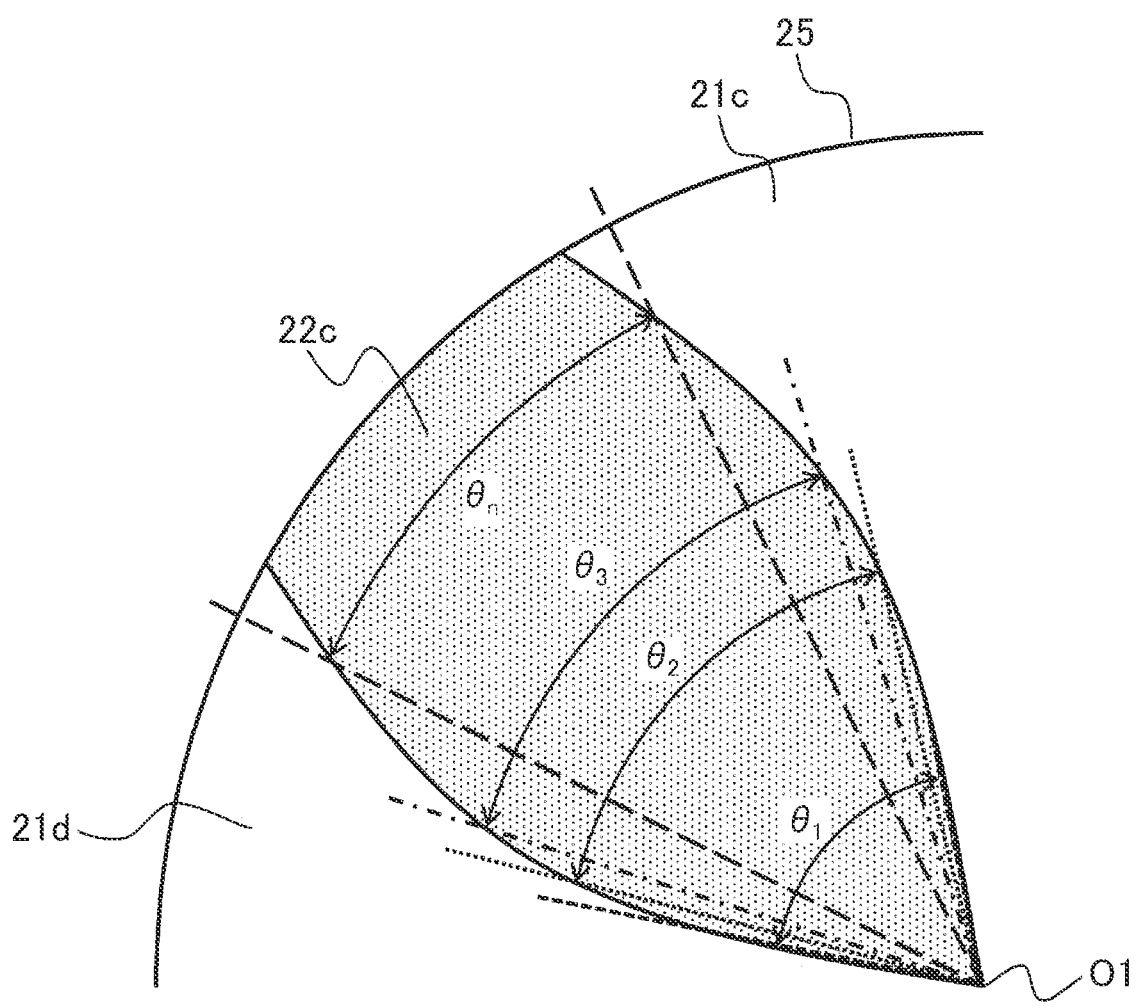
FIG. 5 is an enlarged plan view of one of projections of the magnetic device according to the first embodiment.
Figure 6:
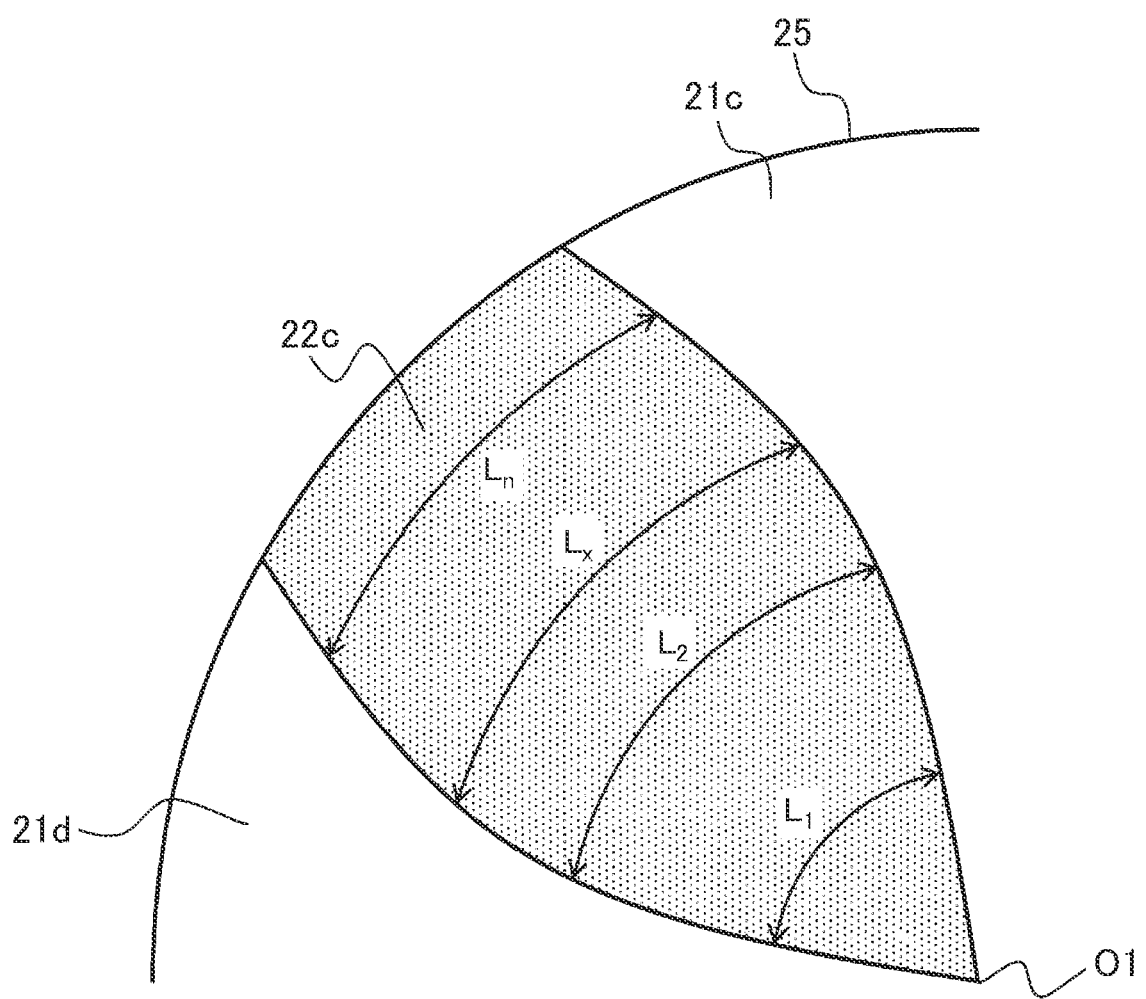
FIG. 6 is an enlarged plan view of one of the projections of the magnetic device according to the first embodiment.
Figure 7:
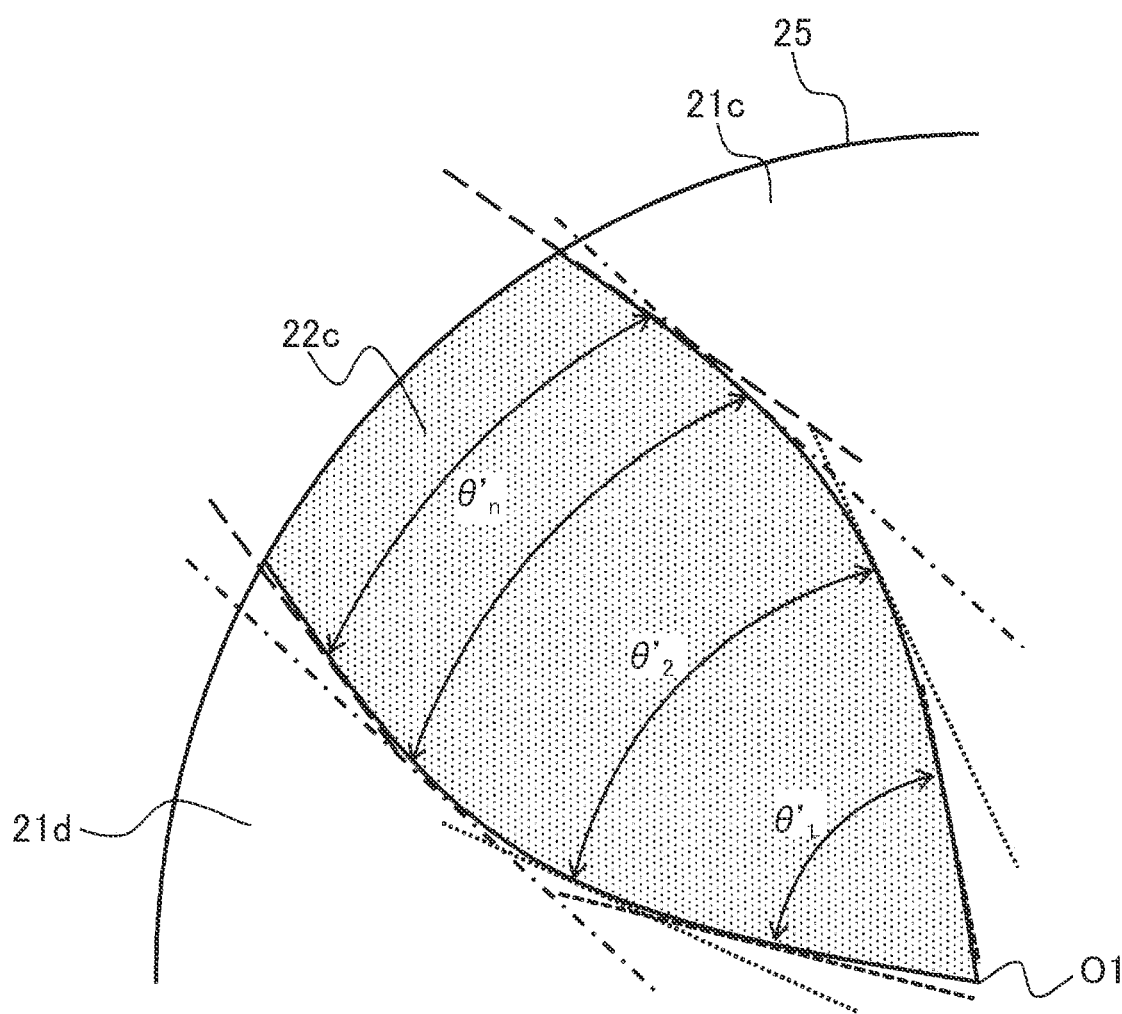
FIG. 7 is an enlarged plan view of one of the projections of the magnetic device according to the first embodiment.

FIG. 1 is a block diagram of a particle therapy system according to the first embodiment. FIG. 2 is a perspective view of a magnetic device placed in the accelerator. FIG. 3 is a cross sectional view of the magnetic device taken along a vertical plane. FIG. 4 is a plan view of the magnetic device viewed from a middle plane. FIGS. 5 to 7 are enlarged plan views of one of projections of the magnetic device.

First, the overall structure of the particle therapy system will be described with reference to FIG. 1.

In FIG. 1, a particle therapy system 1001 is installed on the floor surface of a building (not shown in the drawing). This particle therapy system 1001 includes an ion beam generator 1002, a beam transport system 1013, a rotating gantry 1006, an irradiation system 1007, and a control system 1065.

The ion beam generator 1002 has an ion source 1003 and an accelerator 1004 to which this ion source 1003 is connected. The detail of the accelerator 1004 will be described later.

The beam transport system 1013 has a beam path 1048 that reaches the irradiation system 1007, and the beam transport system 1013 is formed of a plurality of quadrupole electromagnets 1046, a bending magnet 1041, a plurality of quadrupole electromagnets 1047, a bending magnet 1042, quadrupole electromagnets 1049 and 1050, and bending magnets 1043 and 1044 placed on the beam path 1048 in this order from the accelerator 1004 toward the irradiation system 1007.

A part of the beam path 1048 of the beam transport system 1013 is installed on the rotating gantry 1006, and the bending magnet 1042, the quadrupole electromagnets 1049 and 1050, and the bending magnets 1043 and 1044 are also on the rotating gantry 1006. The beam path 1048 is connected to an extraction channel 1019 provided on the accelerator 1004.

The rotating gantry 1006 is formed such that the rotating gantry 1006 is rotatable about a rotation axis 1045, and is a rotation system that turns the irradiation system 1007 about the rotation axis 1045.

The irradiation system 1007 includes two scanning magnets 1051 and 1052, a beam position monitor 1053, and a dose monitor 1054. The scanning magnets 1051 and 1052, the beam position monitor 1053, and the dose monitor 1054 are placed along the center axis of the irradiation system 1007, i.e., along the beam axis. The scanning magnets 1051 and 1052, the beam position monitor 1053, and the dose monitor 1054 are placed in the casing (not shown in the drawing) of the irradiation system 1007.

The beam position monitor 1053 and the dose monitor 1054 are placed on the downstream of the scanning magnets 1051 and 1052. The scanning magnet 1051 and the scanning magnet 1052 bend ion beams, and scan the ion beams in directions orthogonal to each other in a plane vertical to the center axis of the irradiation system 1007. The beam position monitor 1053 measures the passing position of an irradiation beam. The dose monitor 1054 measures the dose of the irradiation beam.

The irradiation system 1007 is mounted on the rotating gantry 1006, and is placed on the downstream of the bending magnet 1044.

On the downstream side of the irradiation system 1007, a treatment table 1055 on which a patient 1056 lies down is placed such that the treatment table 1055 is opposed to the irradiation system 1007.

The control system 1065 has a central control unit 1066, an accelerator-transport-line control apparatus 1069, a scan control apparatus 1070, a rotating control apparatus 1088, and a database 1072.

The central control unit 1066 has a central processing unit (the CPU) 1067 and a memory 1068 connected to the CPU 1067. The accelerator-transport-line control apparatus 1069, the scan control apparatus 1070, the rotating control apparatus 1088, and the database 1072 are connected to the CPU 1067 in the central control unit 1066.

The particle therapy system 1001 further has a treatment planning system 1073. The treatment planning system 1073 is connected to the database 1072. In the particle therapy system 1001, the irradiation energy, irradiation angle, or other parameter of a particle beam is created as a treatment plan by the treatment planning system 1073 prior to the irradiation of the particle beam, and irradiation is performed based on the treatment plan.

The CPU 1067 of the central control unit 1066 reads various operation control programs relating to the irradiation of devices constituting the particle therapy system 1001 from the treatment plan stored on the database 1072, executes the read programs, outputs commands through the accelerator-transport-line control apparatus 1069, the scan control apparatus 1070, and the rotating control apparatus 1088, and thus controls the operation of the devices in the particle therapy system 1001.

Note that the control process of the operation to be performed may be collected on one program, may be separated into a plurality of programs, or may be the combination of these. A part or all the programs may be implemented on dedicated hardware, or may be modularized. Furthermore, various programs may be installed on the devices via a program distribution server or an external storage medium.

The control apparatuses may be independent apparatuses that are connected to each other via a cable or wireless network, or two or more control apparatuses may be integrated with each other.

A beam current meter 1098 includes a moving device 1017 and a position detector 1039.

A radiofrequency power supply 1036 inputs electric power to a radiofrequency acceleration cavity 1037 installed in the accelerator 1004 through a waveguide 1010, and excites a radiofrequency electric field that accelerates a beam across an electrode and a ground electrode connected to the radiofrequency acceleration cavity 1037. In the accelerator 1004 according to the present embodiment, the resonance frequency of the radiofrequency acceleration cavity 1037 has to be modulated corresponding to the energy of the beam. In order to modulate the frequency, inductance or electrostatic capacitance only has to be adjusted.

For the adjustment method for inductance or electrostatic capacitance, a publicly known method can be used. For example, in the case in which electrostatic capacitance is adjusted, a variable capacitance capacitor is connected to the radiofrequency acceleration cavity 1037 for control.

Next, the detail of the magnetic device 1 that forms the accelerator 1004 will be described with reference to FIG. 2 and the drawing after FIG. 2.

The magnetic device 1 has an upper return yoke 4 and a lower return yoke 5 in a nearly disc-like shape viewed from the vertical direction as shown in FIG. 2.

The upper return yoke 4 and the lower return yoke 5 have a shape in nearly vertical surface symmetry with respect to a middle plane 2. The middle plane 2 passes approximately the center of the magnetic device 1 in the vertical direction, and is nearly matched with the orbit face that is drawn by ions in acceleration. The upper return yoke 4 and the lower return yoke 5 have a shape vertical to the middle plane 2 and in surface symmetry with respect to a vertical plane 3 that is a plane vertically passing the center of the middle plane 2 of the magnetic device 1.

Note that in FIG. 2, the intersecting part of the middle plane 2 to the magnetic device 1 is depicted by an alternate long and short dash line, and the intersecting part of the vertical plane 3 to the magnetic device 1 is depicted by a broken line.

On the upper return yoke 4, the ion source 1003 is placed.

As shown in FIG. 3, in a space surrounded by the upper return yoke 4 and the lower return yoke 5, a coil 6 is placed in surface symmetry with respect to the middle plane 2.

Note that in the first embodiment, the ion source 1003 is installed on the outside of the magnetic device 1, and a through hole 24 is provided corresponding to the ion source 1003 as an external ion source is assumed. However, the ion source 1003 may be installed in the inside of the magnetic device 1.

The coil 6 is connected to a coil excitation power supply 1057 by a coil drawing wire 1022 shown in FIG. 1. On the inner side of the coil 6 in the space surrounded by the upper return yoke 4 and the lower return yoke 5, a vacuum chamber 7 is provided.

The coil 6 is a superconducting coil, and the coil 6 is installed in the inside of a cryostat (not shown in the drawing), and cooled due to heat transfer from a coolant, such as liquid helium, or a refrigerator (not shown in the drawing).

In the inside of the vacuum chamber 7, an upper magnetic pole 8 is placed on the face of the upper return yoke 4, opposite to the lower return yoke 5 and a lower magnetic pole 9 is placed on the face of the lower return yoke 5 opposite to the upper return yoke 4 in surface symmetry with respect to the middle plane 2, and the upper magnetic pole 8 and the lower magnetic pole 9 are respectively coupled to the upper return yoke 4 and the lower return yoke 5.

The upper return yoke 4, the lower return yoke 5, the upper magnetic pole 8, or the lower magnetic pole 9 is made of pure iron whose impurity concentration is decreased, low-carbon steel, and any other material, for example. The vacuum chamber 7 is made of stainless steel, for example. The coil 6 is made a superconductor, such as NbTi.

A space in which an ion beam is circled and accelerated is formed between the upper magnetic pole 8 and the lower magnetic pole 9.

In this space, magnetic field correction electromagnets 11, 12, 13, and 14 are placed with respect to the middle plane 2. The magnetic field correction electromagnets 11, 12, 13, and 14 are placed in surface symmetry with respect to the middle plane 2, and are connected to an extraction electromagnet power supply 1040 by an extraction electromagnet drawing wire 1023 shown in FIG. 1 through a through hole 16.

The extraction channel 1019 includes an electromagnet (not shown in the drawing), and is connected to an extraction channel power supply 1082 shown in FIG. 1 through a through hole 15. Carrying an electric current through the electromagnet included in the extraction channel 1019 from the extraction channel power supply 1082 adjusts the ion beam that has reached the extraction channel 1019, and the ion beam is sent delivered to the beam transport system 1013.

FIG. 4 is a plan view of an opposing face 10 viewed from the middle plane 2. The magnetic device 1 has a structure in surface symmetry with respect to the middle plane 2, and in the following, the detail of the structure of the magnetic device 1 will be described with reference to FIGS. 3 and 4.

On the faces of the upper magnetic pole 8 and the lower magnetic pole 9 opposite to the middle plane 2, recesses 21*a*, 21*b*, 21*c*, and 21*d*, and projections 22*a*, 22*b*, 22*c*, and 22*d* are respectively formed. The recesses 21*a*, 21*b*, 21*c*, and 21*d* and the projections 22*a*, 22*b*, 22*c*, and 22*d* are alternately placed along the circling direction of a beam orbit 23.

The recesses 21*a*, 21*b*, 21*c*, and 21*d* and the projections 22*a*, 22*b*, 22*c*, and 22*d* may be ones integrally with the upper magnetic pole 8 or the lower magnetic pole 9, or may be formed as separate members and then engaged with the surface of the upper magnetic pole 8 or the lower magnetic pole 9 by a publicly known method, such as welding and bolting, in the assembly of the upper magnetic pole 8 or the lower magnetic pole 9. The materials of the recesses 21*a*, 21*b*, 21*c*, and 21*d* and the projections 22*a*, 22*b*, 22*c*, and 22*d* are desirably the same as the material of the upper magnetic pole 8 or the lower magnetic pole 9.

A beam displacement producing magnet 31 (regenerator) is installed near a magnetic pole outer circumferential face 25 of the projection 22*a* adjacent to the recess 21*a* at which the extraction channel 1019 is provided. A beam displacement producing magnet 32 (peeler) is installed near a magnetic pole outer circumferential face 25 of the projection 22*d* adjacent to the recess 21*a* at which the extraction channel 1019 is provided.

A magnetic field distribution generated by the beam displacement producing magnet 31 is desirably designed such that primary magnetic field strength is increased toward the radial direction. A magnetic field distribution generated by the beam displacement producing magnet 32 is desirably designed such that primary magnetic field strength is decreased toward the radial direction.

The beam circling in the above-described space senses a magnetic field (disturbing magnetic field) produced by the beam displacement producing magnets 31 and 32, and thus the beam orbit receives displacement in the direction of the extraction channel 1019.

Note that the beam displacement producing magnets 31 and 32 are not limited to a magnet that produces a magnetic field, and may be an electromagnet.

Furthermore, instead of using the beam displacement producing magnets 31 and 32, an equivalent structure that produces a magnetic field to displace the beam orbit can be provided on the surfaces of the projections 22a and 22d. An example of the structure can include further adding a magnetic substance on the surfaces of the projections 22a and 22d, or processing the surface shapes of the projections 22a and 22d.

A through hole 18 is a through hole for installing the beam transport system 1013 is installed, and a through hole 19 is provided in surface symmetry with the through hole 18 respect to the vertical plane 3 for enhancing the symmetry of the magnetic device to achieve the high accuracy of the magnetic field produced by the magnetic device.

In the following, in order to describe the effect of the structure of the present embodiment, the procedures of designing the magnetic device 1 will be described with reference to FIGS. 5 to 7.

First, in order to determine the size of the magnetic device 1, it is necessary to determine magnetic field strength and the radius of the beam orbit at the highest energy. As the magnitude of the magnetic field produced by the magnetic device 1 is large, the spread of the beam orbit becomes small, and this can reduce the size of the accelerator 1004, and thus the size of the particle therapy system 1001.

In the present embodiment, the magnetic field at the incident point is set to five tesla, and the beam radius at the highest energy is set to one meter. Note that in the present embodiment, the incident point of the beam to be accelerated is matched with the position of the center O1 of the maximum beam energy orbit.

Subsequently, an ideal magnetic field distribution on which the beam stably circles has to be determined. In the present embodiment, in order to converge the beam in the direction vertical to the middle plane 2, the magnetic field was designed based on the principle of weak convergence.

In the accelerator using the principle of weak convergence, an amount referred to as an n-index shown in Equation (1) below is generally used.

[Eq. 1]

$$n = -\frac{\rho}{B}\frac{\partial B}{\partial r} \quad (1)$$

The magnetic field distribution is designed such that the n-index is greater than zero and is two or less. Here, B is the magnetic field on the middle plane 2, $\rho$ is the radius of curvature of the beam orbit, and a magnetic field gradient $\partial B/\partial r$ is the differential of the magnetic field with respect to a direction that is vertical to the beam traveling direction, the direction in which beam energy is increased on the middle plane 2.

In the first embodiment, since the magnetic field strength was set to five tesla and the beam radius at the highest energy (the maximum orbit radius) was set to one meter, $\partial B/\partial r$ had to be −1 T/m or more and smaller than zero. Here, $\partial B/\partial r$ is to −0.5 T/m. Then, the beam radius at the highest energy is one meter, so that the magnetic field on this orbit is 4.5 tesla.

Generally, in circular accelerator that converges the beam based on the principle of weak convergence, in order to produce a magnetic field distribution in axial symmetry, its magnetic pole shape is often in axial symmetry as well. by doing so, the magnetic field B takes a constant value along the beam circling direction. However, the principle of weak convergence does not necessarily request B to be constant in the beam circling direction, and is held also in the case in which B is a mean magnetic field with respect to the beam circling direction. That is, the strength and weakness of the magnetic field may be distributed in the beam circling direction.

Therefore, in the present embodiment, the magnetic field was designed such that the strength and weakness of the magnetic field are distributed in the beam circling direction by four recesses 21a, 21b, 21c, and 21d and four projections 22a, 22b, 22c, and 22d and the mean magnetic field mean in the beam circling direction is decreased as beam energy is increased according to Equation (1).

In a region sandwiched by the upper and lower projections 22a, 22b, 22c, and 22d, since the distance between the upper magnetic pole 8 and the lower magnetic pole 9 becomes short, the magnetic field is increased more than in a region sandwiched between the upper and lower recesses 21a, 21b, 21c, and 21d.

Therefore, as shown in FIG. 5, angle widths $\theta_1$, $\theta_2$, $\theta_2$, . . . , and $\theta_n$ of the projections 22a, 22b, 22c, and 22d become narrow viewed from the center O1 of the beam closed orbit ($\theta_1 > \theta_2 > \theta_3 > $ . . . $ > \theta_n$) as beam energy is increased and comes closer to the magnetic pole outer circumferential face 25.

In the present embodiment, narrowing the angle widths $\theta_1$, $\theta_2$, $\theta_2$, . . . , and $\theta_n$ of the projections 22a, 22b, 22c, and 22d in this manner means that the angle widths of the recesses 21a, 21b, 21c, and 21d when viewed from the center O1 of the beam closed orbit spread as beam energy is increased.

For a first approximation, it is thought that the magnetic fields of the region sandwiched between the recesses 21a, 21b, 21c, and 21d and the region sandwiched between the projections 22a, 22b, 22c, and 22d are constant values, and the angle width only has to be adjusted such that the angle widths of the projections 22a, 22b, 22c, and 22d are reduce as the angle widths are matched with a decrease in the mean magnetic field determined by Equation (1).

That is, when the magnetic field in the region sandwiched between the recesses 21a, 21b, 21c, and 21d is By, the magnetic field in the region sandwiched between the projections 22a, 22b, 22c, and 22d is $B_h$, $\theta$ only has to be determined from the relationship in Equation (2) bellow.

[Eq. 2]

$$\frac{\theta(r)}{2\pi} = \frac{B(r) - B_v}{B_h - B_v} \quad (2)$$

Here, the unit of $\theta$ is radian, and $B_v < B(r) < B_h$.

As shown in FIG. 6, in the projections 22a, 22b, 22c, and 22d thus designed, a relationship is held in which distances $L_1, L_2, \ldots$, and $L_n$ through which the beam to be accelerated passes each of the projections 22a, 22b, 22c, and 22d are increased with an increase in beam energy ($L_x > L_2 > L_1$) and then decreased ($L_x > L_n$). Note that in FIG. 6, only the projection 22c is shown as a representative. The same thing is applied to FIG. 7 as well.

Furthermore, as shown in FIG. 7, in the projections 22a, 22b, 22c, and 22d, an angle between the tangent of the boundary between the projection 22c and the recess 21d and the tangent of the boundary between the projection 22c and the recess 21c on the opposite side of the projection 22c and the recess 21d is decreased as beam energy is increased ($\theta'^1 > \theta'_2$). After that, a relationship is held in which these two tangents are in parallel with each other, and then the angle is increased.

In the magnetic field thus obtained, since the mean magnetic field to the beam at the highest energy can have 4.5 tesla, which is the same value in the case in which the magnetic pole is in an axial symmetry shape, the size of the accelerator is equivalent. On the other hand, in the magnetic pole shape in axial symmetry, the magnetic field to the beam at the highest energy is uniformly 4.5 tesla. However, in the embodiment, the magnetic field is less than 4.5 tesla at the recess, and exceeds 4.5 tesla at the projection.

Therefore, the inlet of the extraction channel 1019 that extracts the beam accelerated to a predetermined energy to outside of the accelerator 1004 is installed near the magnetic pole outer circumferential face 25 of the recess 21a, and thus the magnetic field that has to be produced by the extraction channel 1019 for beam extraction can be made smaller than the magnetic pole shape in axial symmetry, and beam extraction can be made easy.

Next, the effect of the present embodiment will be described.

The above-described particle therapy system 1001 according to the first embodiment of the present invention includes the accelerator 1004. In this system, the accelerator 1004 includes the radiofrequency acceleration cavity 1037 that enables the modulation of the frequency of the radiofrequency electric field to accelerate a beam, and the magnetic device 1 that produces a static magnetic field. The magnetic device 1 has the upper return yoke 4, the lower return yoke 5, and a pair of the upper magnetic pole 8 and the lower magnetic pole 9 fixed to the upper return yoke 4 and the lower return yoke 5. The pair of the upper magnetic pole 8 and the lower magnetic pole 9 are placed at positions surface symmetry with respect to the middle plane 2 located in the space sandwiched between the pair of the upper magnetic pole 8 and the lower magnetic pole 9. On the faces opposite to the middle plane 2 between the upper magnetic pole 8 and the lower magnetic pole 9, the recesses 21a, 21b, 21c, and 21d and the projections 22a, 22b, 22c, and 22d are alternately placed along the beam circling direction. On the outer circumferential region of the recess 21a on the upper magnetic pole 8 and the lower magnetic pole 9, the inlet of the extraction channel 1019 that extracts the beam accelerated to a predetermined energy to outside the accelerator 1004 is provided. Furthermore, in the projections 22a, 22b, 22c, and 22d, the angle widths θ of the projections 22a, 22b, 22c, and 22d when viewed from the center O1 of the beam closed orbit are narrowed as beam energy is increased. The distance at which the beam to be accelerated passes each of the projections 22a, 22b, 22c, and 22d is increased as beam energy is increased, and then decreased. moreover, an angle between the tangent of the boundary between the projections 22a, 22b, 22c, and 22d and the recesses 21a, 21b, 21c, and 21d and the tangent of the boundary between the projections 22a, 22b, 22c, and 22d and the recesses 21a, 21b, 21c, and 21d on the opposite side is increased after the angle is decreased as beam energy is increased.

Thus, also in the case in which in the accelerator including the radiofrequency acceleration cavity 1037 that enables frequency modulation, the primary magnetic field is increased, the beam can be stably accelerated without increasing the size of the accelerator. The magnetic field strength of the magnetic pole in the outer circumferential region in which the inlet of the extraction channel 1019 that is an extraction port for the accelerated beam is placed can be weakened. Thus, a small-sized accelerator including a magnetic device that easily extracts a beam can be provided with no use of difficult methods, such as achieving high performance of septum and an increase in the size of septum.

Since the mean value of the magnetic field produced by the magnetic device 1 along the beam circling direction is decreased as beam energy is increased, the magnetic field strength of the magnetic pole in the outer circumferential region in which the inlet of the extraction channel 1019 is placed can be further weakened, and thus the beam can be more easily extracted.

Moreover, even though the incident point of the beam to be accelerated is matched with the position of the center O1 of the maximum beam energy orbit, the magnetic field strength of the magnetic pole in the outer circumferential region in which the inlet of the extraction channel 1019 is placed is weakened more than in a conventional accelerator, and thus an accelerator that more easily extracts a beam is provided.

Since the beam displacement producing magnets 31 and 32 that feed a magnetic field to displace the beam orbit are provided in the outer circumferential regions of the projections 22a and 22d on the upper magnetic pole 8 and the lower magnetic pole 9, the projections 22a and 22d being adjacent to the recess 21a provided with the extraction channel 1019, the betatron oscillation on the closed orbit plane to a beam that takes specific energy desired to be extracted can be made destabilized, and thus the effect can be obtained in which a beam at given energy can be more easily extracted. Such an accelerator is suited to a particle therapy system that can achieve an irradiation dose rate and can improve the treatment throughput of patients.

Second Embodiment

A particle beam accelerator and a particle therapy system according to a second embodiment of the present invention will be described with reference to FIGS. 8 to 12. Components the same as ones of the first embodiment are designated with the same reference signs, and the description is omitted.

Figure 8:
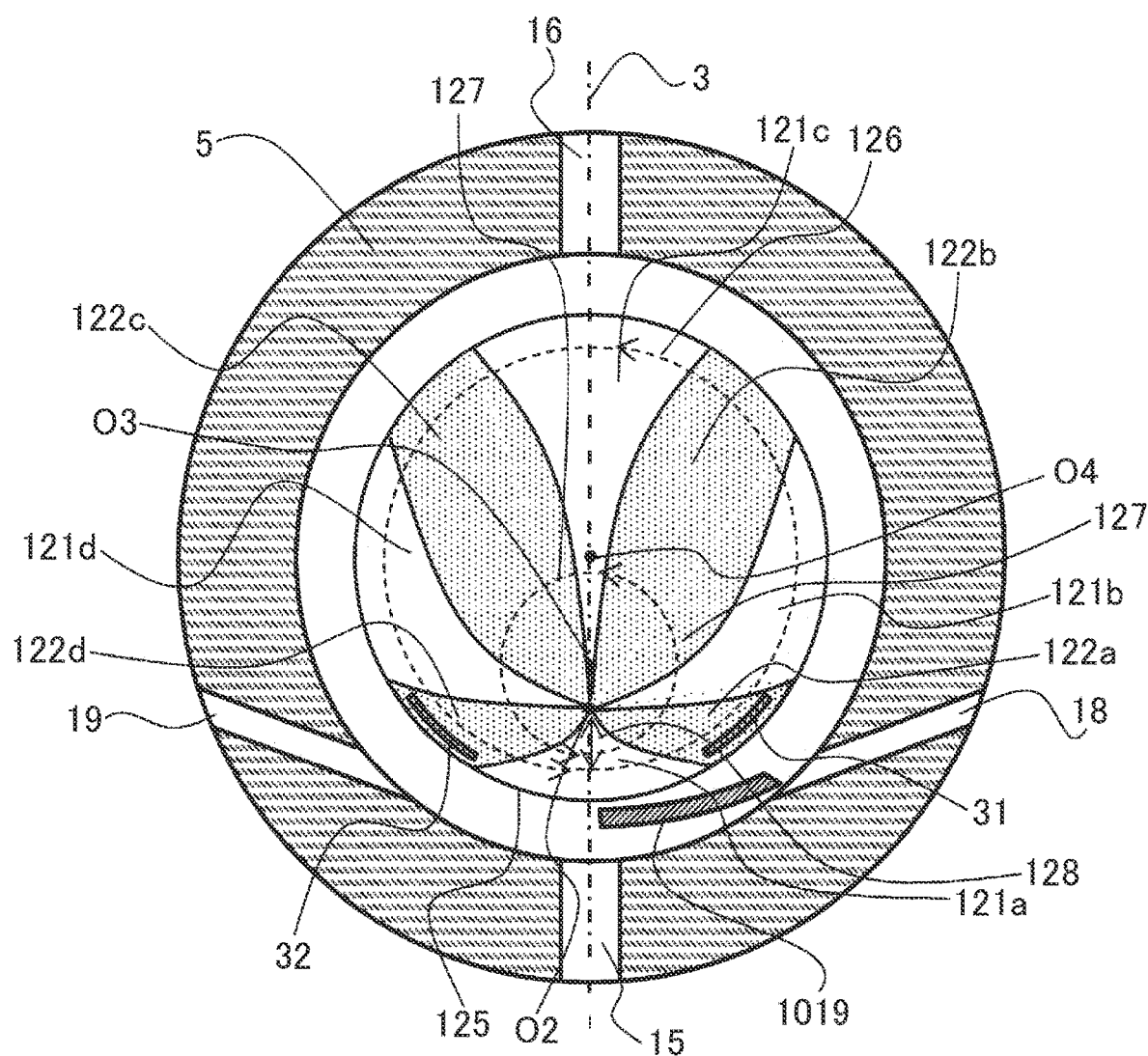
FIG. 8 is a plan view of a magnetic device according to a second embodiment of the present invention viewed from a middle plane.

FIG. 8 is a plan view of a magnetic device according to the second embodiment viewed from a middle plane. FIGS. 9 to 12 are enlarged plan views of one of the projections of the magnetic device.

The particle beam accelerator according to the present embodiment is different from the particle beam accelerator according to the foregoing first embodiment is that the shapes of the opposing faces of an upper magnetic pole and a lower magnetic pole in the magnetic device are different. In the following, the description will be made with reference to FIG. 8 and the drawings after FIG. 8.

In the particle beam accelerator, when the kinetic energy of a beam is K, rest energy is $E_0$, the velocity of light is c, and the charge number of a charged particle is q, the relationship of Equation (3) below is held.

[Eq. 3]

$$B\rho = \frac{\sqrt{K(K+2E_0)}}{cq} \quad (3)$$

When Equation (3) above and Equation (2) described in the first embodiment are combined, θ can be reviewed from the function of a radial distance r to the function of K. Particularly, in the case in which the center of the beam orbit is matched with the center of the magnetic pole, r=ρ. However, in the second embodiment, the case is shown in which the center of the beam orbit is not matched with the center of the magnetic pole and the positions of an incident point O2 of the beam to be accelerated, a center O4 of the maximum beam energy orbit, and centers O3, O5, and O6 of the closed orbits of a beam in the accelerator are different.

FIG. 8 is a plan view of an opposing face 10 according to the second embodiment viewed from a middle plane 2. Structures and the like similar to the first embodiment are shown appropriately using the same numbers.

In FIG. 8, the beam incident point is O2, the orbit center of a beam orbit 126 at the highest energy is O4, the orbit center of a beam orbit 127b at energy in the middle between the beam incident point and the beam orbit 127b is O3, and the centers of the beam orbit of energy accelerated from the middle are O5 and O6.

As described above, the beam orbit center O4 at the highest energy is not matched with the incident point O2, and the incident point O2 is displaced to the beam inlet direction of an extraction channel 1019. When the center of the beam orbit is displaced as described above, the beam orbit at low energy can be made close to the inlet of the extraction channel 1019. Thus, the beam accelerated to the highest energy as well as energy beams below the highest energy can be easily extracted from the extraction channel 1019.

In the second embodiment, a beam orbit width 128 from incident energy to the beam orbit was set to 0.1 meter. Then, similarly to the first embodiment, when ∂B/∂r is set to −1.0 T/m, the magnetic field to the highest energy is 4.9 tesla.

Figure 9:
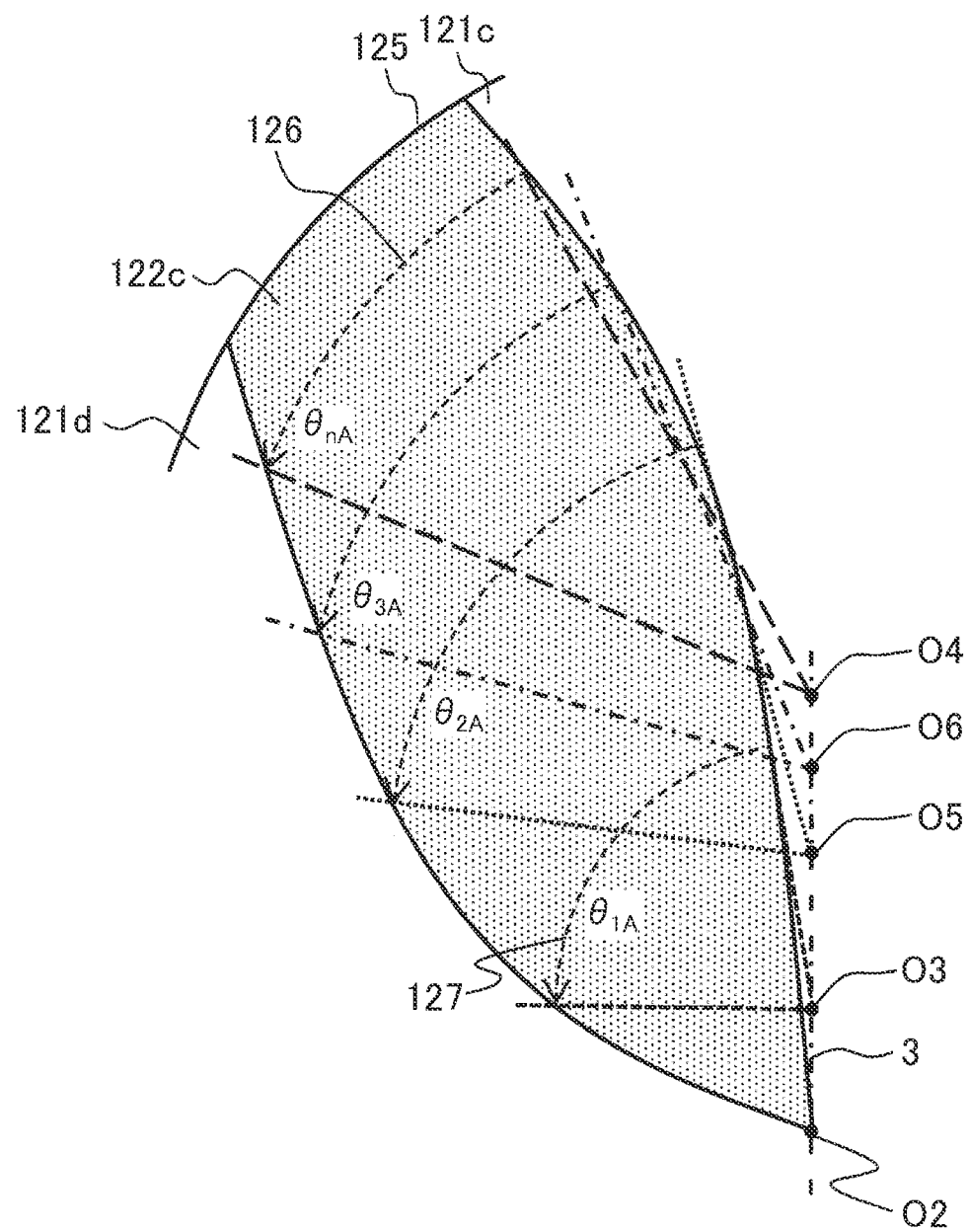
FIG. 9 is an enlarged plan view of one of projections of the magnetic device according to the second embodiment.

As shown in FIG. 9, also in this embodiment 2, angle widths $\theta_{1A}, \theta_{2A}, \theta_{3A}, \ldots,$ and $\theta_{nA}$ of a projection 122c when viewed from the centers O3, O5, O6, and O4 of the beam closed orbit are narrowed as beam energy is increased according to Equation (2) and Equation (3) ($\theta_{1A} > \theta_{2A} > \theta_{3A} > \ldots > \theta_{nA}$).

Figure 10:
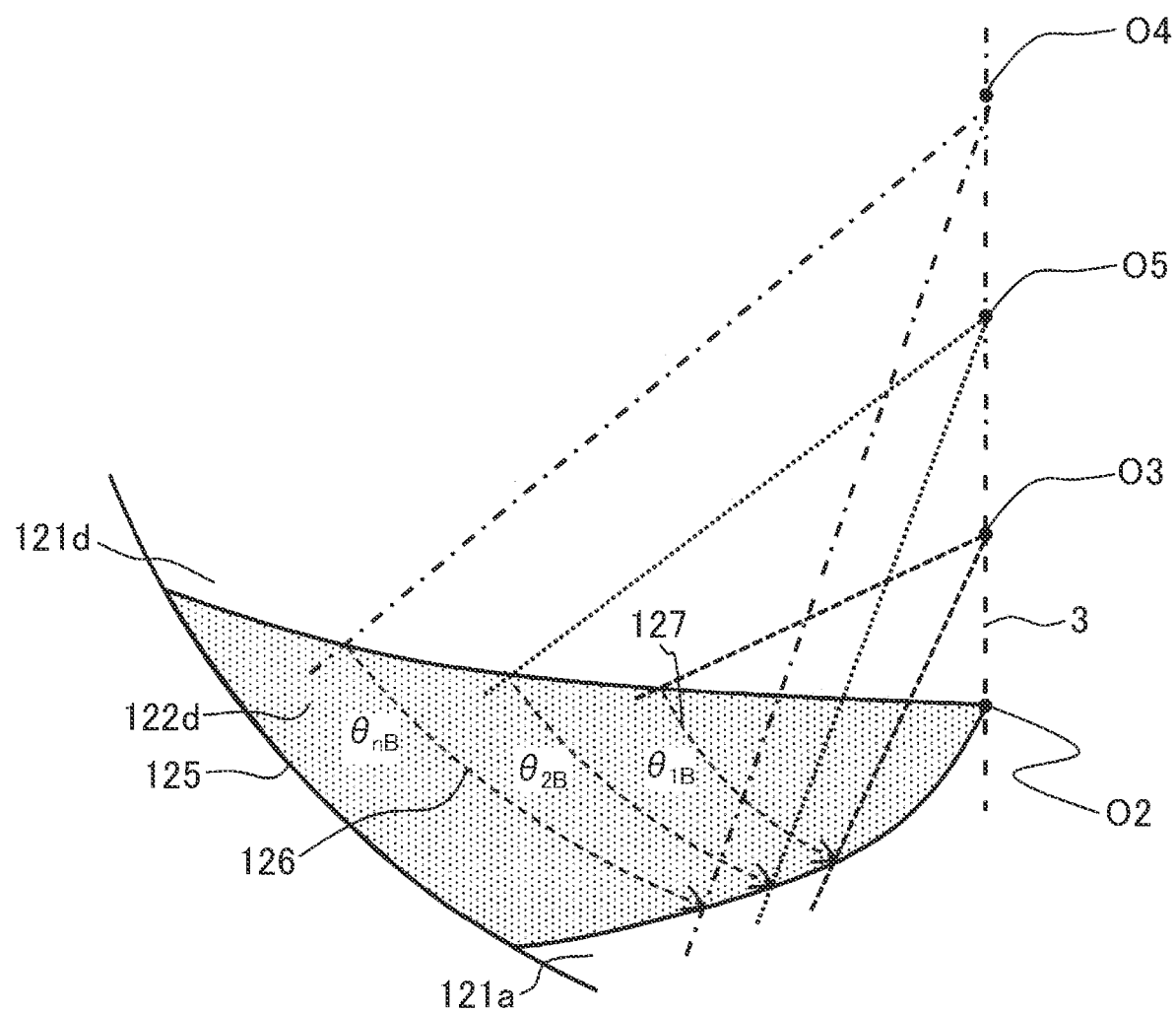
FIG. 10 is an enlarged plan view of one of the projections of the magnetic device according to the second embodiment.

Similarly, as shown in FIG. 10, angle widths $\theta_{1B}, \theta_{2B}, \ldots,$ and $\theta_{nB}$ of a projection 122d when viewed from the centers O3, O5, and O4 of the beam closed orbit are narrowed as beam energy is increased according to Equation (2) and Equation (3) ($\theta_{1B} > \theta_{2B} > \ldots > \theta_{nB}$).

Figure 11:
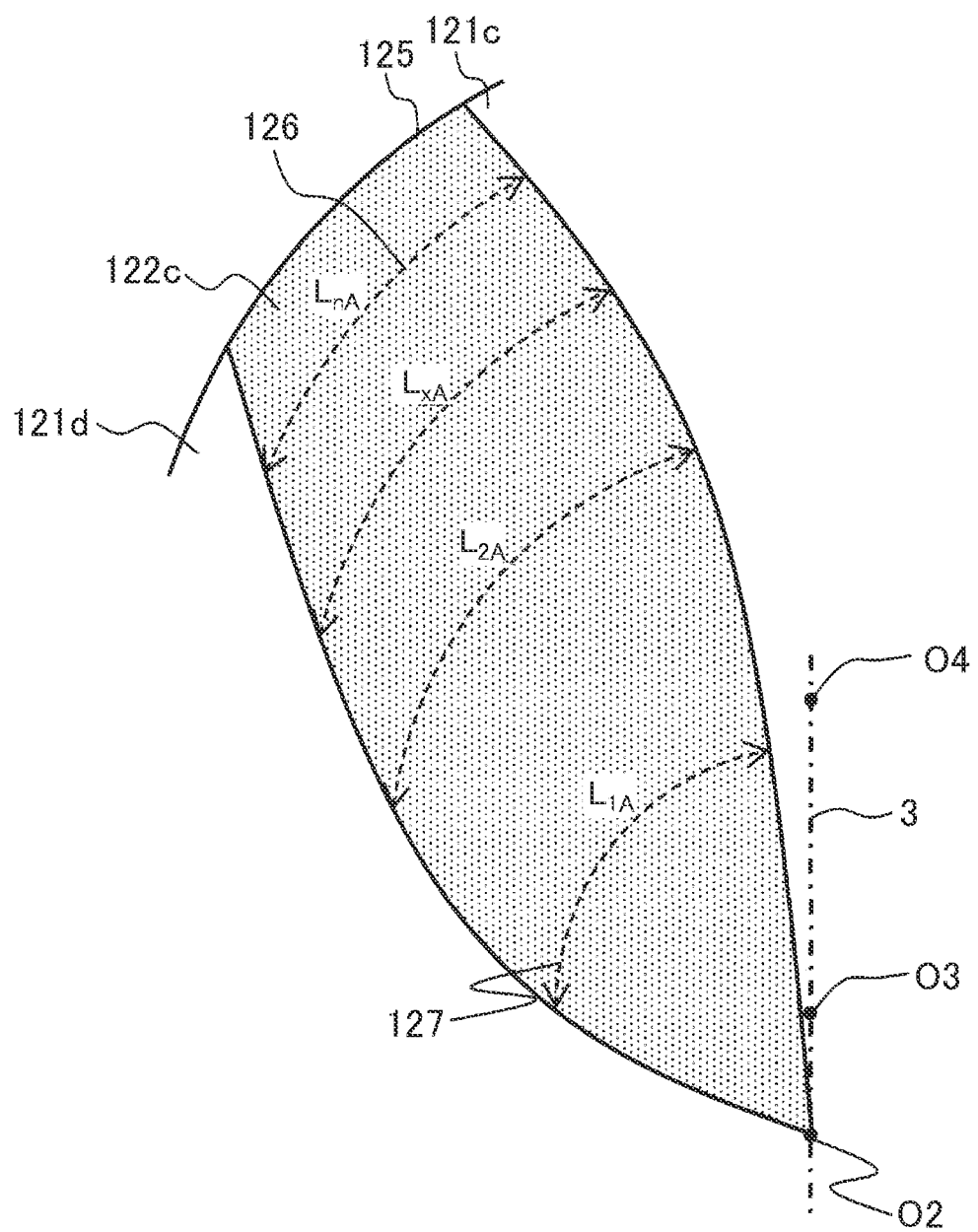
FIG. 11 is an enlarged plan view of one of the projections of the magnetic device according to the second embodiment.

As shown in FIG. 11, in the projection 122c thus designed, a relationship is held in which distances $L_{1A}, L_{2A}, \ldots,$ and $L_{nA}$ at which the beam to be accelerated passes one projection 122c are increased as beam energy is increased ($L_{2A} > L_{1A}$), and then decreased ($L_{2A} > L_{xA} > L_{nA}$).

Figure 12:
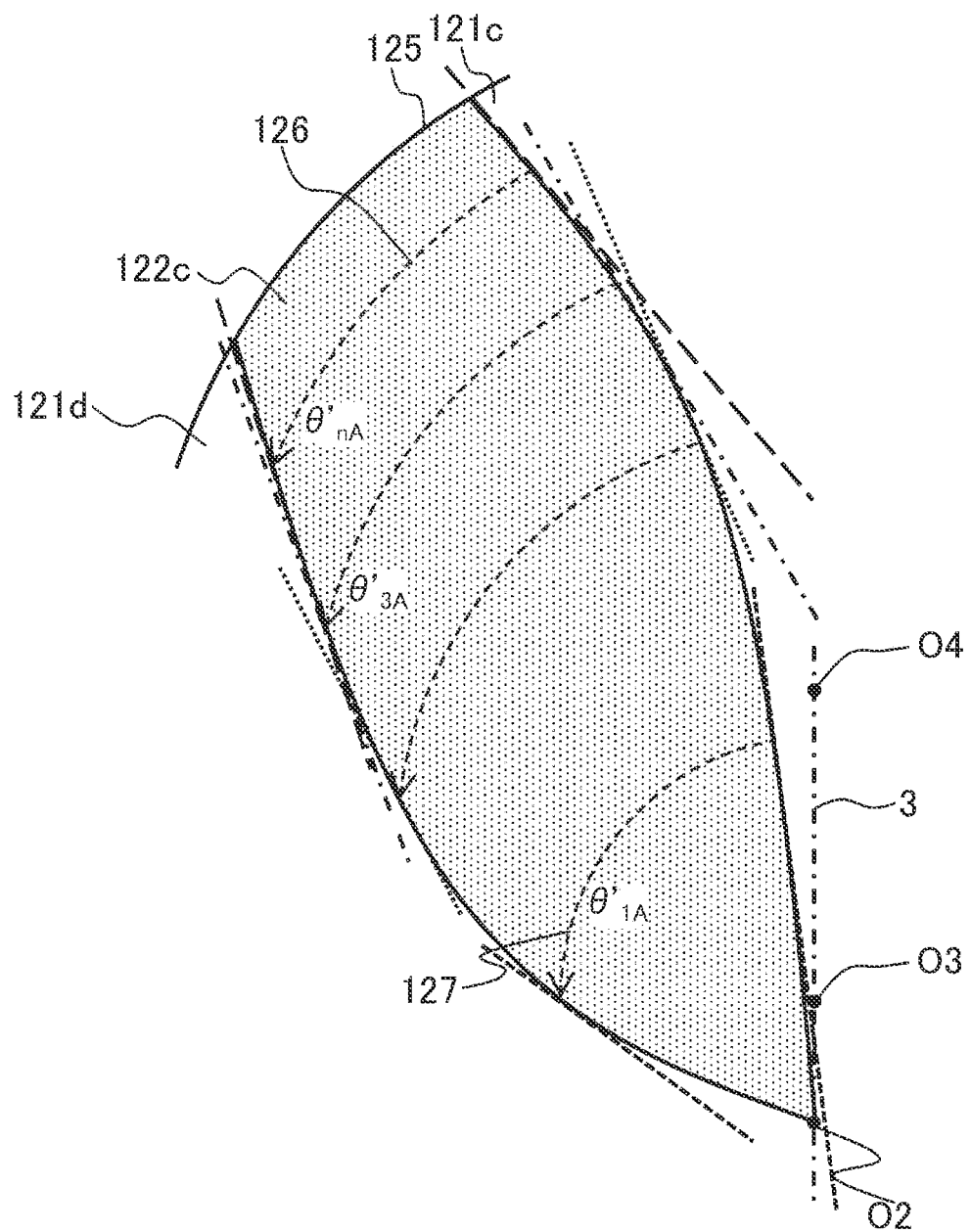
FIG. 12 is an enlarged plan view of one of the projections of the magnetic device according to the second embodiment.

Furthermore, as shown in FIG. 12, in the projection 122c, a relationship is held in which an angle between the tangent of the boundary between the projection 122c and a recess 121d and the tangent of the boundary between the projection 122c and a recess 121c on the opposite side of the projection 122c and a recess 121d is decreased as beam energy is increased, these two tangents are then in parallel with each other, and then the angle is increased ($\theta'_{3A} > \ldots > \theta'_{nA}$).

Although not shown in the drawings, a projection 122b in a shape in symmetry with the projection 122c with respect to a vertical plane 3 is also similar to the projection 122c. A projection 122a in a shape in symmetry with the projection 122d with respect to the vertical plane 3 is also similar to the projection 122d.

In the magnetic field thus obtained, since the mean magnetic field along the beam circling direction can be set to the same value as 4.9 tesla in the case in which the magnetic pole is formed in an axial symmetry shape, the size of the accelerator is equivalent to the case of an axial symmetry shape.

On the other hand, in the magnetic pole shape in axial symmetry, the magnetic field to the beam at the highest energy is constant as 4.9 tesla along the beam circling direction. However, the magnetic field is less than 4.9 tesla in the second embodiment, in the recesses 121a, 121b, 121c, and 121d, and the magnetic field exceeds 4.9 tesla in the projections 122a, 122b, 122c, and 122d.

Therefore, also in the present embodiment, the inlet of the extraction channel 1019 that extracts the beam accelerated to a predetermined energy to outside the accelerator 1004 is installed near a magnetic pole outer circumferential face 125 of the recess 121a, thus the magnetic field that has to be produced by the extraction channel 1019 for beam extraction can be made smaller than the magnetic pole shape in axial symmetry, and beam extraction can be made easy.

The other structures and operations are nearly the same as those of the particle beam accelerator and the particle therapy system of the foregoing first embodiment, and the detail is omitted.

Also in the particle beam accelerator according to the second embodiment of the present invention, the effect almost similar to that of the particle beam accelerator according to the foregoing first embodiment can be obtained.

The position of the incident point O2 of the beam to be accelerated is different from the position of the center O1 of the maximum beam energy orbit, and thus a region in which the beam closed orbits are dense can be provided on the magnetic pole outer circumferential part on which the inlet of the extraction channel 1019 is installed. The magnetic field that has to be produced by the extraction channel 1019 for beam extraction can be made smaller than the case in which the magnetic field has a magnetic pole shape in axial symmetry. Accordingly, the beam accelerated to a predetermined energy can be more easily extracted.

Other

Note that the present invention is not limited to the above-described embodiments, and includes various exemplary modifications. The above-described embodiments are described in detail for easily understanding the present invention, and are not limited to ones including all the configurations.

A part of the configuration of an embodiment can be replaced by the configuration of another embodiment, and the configuration of another embodiment can be added to the configuration of an embodiment. In regard to a part of the configurations of the embodiments, another configuration can also be added, removed, and replaced.

For example, in the description of the first and the second embodiments, particles to be accelerated are not specified particularly. That is, even though protons are supplied from the ion source 1003 or carbon ions are supplied from the ion source 1003, the frequency of the radiofrequency acceleration cavity 1037 is adjusted being matched with the particles to be accelerated, and thus a beam cam be stably accelerated and circled. The particles to be accelerated are not limited to the protons or carbon ions described above, and can be heavy particle ions, such as helium ions, other than carbon ions.

In the description of the first and the second embodiments, the numbers of the recesses and the projections provided on the upper magnetic pole 8 or the lower magnetic pole 9 are four. However, the numbers of the recesses and the projections are not limited to four, and a magnetic field that causes the beam to stably circle can be produced when the number is an integer of three or more.

The case is described in which the particle therapy system 1001 includes the beam transport system 1013. However, the particle therapy system can be directly connected to the ion beam generator and the rotating gantry or the irradiation system with no provision of the beam transport system.

The case is described in which the rotating gantry 1006 is used as a system for irradiation of particle beams used for treatment. However, a fixed irradiation system can be used. The number of the irradiation system for use is not limited to one, and a plurality of irradiation systems can be provided.

The case of a scanning method using the scanning magnets 1051 and 1052 is described as the irradiation method. However, irradiation methods are also applicable to the present invention in which the particle beam distribution is spread and then a dose distribution matched with the shape of a target using a collimator or a bolus, such as a Wobbler method or a double scattering method.

In the case is described in which the accelerator is used for particle beam therapy. However, the applications of the accelerator are not limited to particle beam therapy, and the accelerator can be used for high energy experiment or for creating PET (Positron Emission Tomography) drags, for example.

REFERENCE SIGNS LIST

1: magnetic device
2: middle plane
3: vertical plane
4: upper return yoke
5: lower return yoke
6: coil
7: vacuum chamber
8: upper magnetic pole
9: lower magnetic pole
11, 12, 13, 14: magnetic field correction electromagnet
15, 16, 18, 19, 24: through hole
20: symmetry axis
21a, 21b, 21c, 21d, 121a, 121b, 121c, 121d: recess
22a, 22b, 22c, 22d, 122a, 122b, 122c, 122d: projection
23, 126, 127: beam orbit
25, 125: magnetic pole outer circumferential face
128: beam orbit width
31,32: beam displacement producing magnet
1001: particle therapy system
1004: accelerator (particle beam accelerator)
1019: extraction channel
1037: radiofrequency acceleration cavity

The invention claimed is:

1. A particle beam accelerator comprising:
an acceleration cavity that enables modulation of a frequency of radiofrequency electric field to accelerate a beam; and
a magnetic device that produces a static magnetic field,
wherein: the magnetic device has a return yoke and a pair of magnetic poles fixed to the return yoke;
the pair of magnetic poles are placed at positions in surface symmetry with respect to a middle plane in a space sandwiched between the pair of magnetic poles;
on a face opposite to the middle plane of the magnetic pole, a recess and a projection are alternately placed along a beam circling direction;
in the projection, an angle width of the projection when viewed from a center of a beam closed orbit is narrowed as beam energy is increased; and
in a magnetic pole outer circumferential region of the recess, an inlet of an extraction channel from which a beam accelerated to a predetermined energy is extracted to outside the particle beam accelerator is provided.

2. The particle beam accelerator according to claim 1, wherein a mean value of a magnetic field produced by the magnetic device along the beam circling direction is decreased as beam energy is increased.

3. The particle beam accelerator according to claim 1, wherein an incident point of a beam to be accelerated is different from a position of a center of a maximum beam energy orbit.

4. The particle beam accelerator according to claim 1, wherein an incident point of a beam to be accelerated is matched with a position of a center of a maximum beam energy orbit.

5. The particle beam accelerator according to claim 1, wherein in the magnetic pole outer circumferential region of the projection adjacent to the recess on which the extraction channel is provided, a magnet configured to feed a magnetic field to displace a beam orbit is provided.

6. A particle beam accelerator comprising:
an acceleration cavity that enables modulation of a frequency of radiofrequency electric field to accelerate a beam; and
a magnetic device that produces a static magnetic field,
wherein: the magnetic device has a return yoke and a pair of magnetic poles fixed to the return yoke;
the pair of magnetic poles are placed at positions in surface symmetry with respect to a middle plane in a space sandwiched between the pair of magnetic poles;
on a face opposite to the middle plane of the magnetic pole, a recess and a projection are alternately placed along a beam circling direction;
in the projection, a distance at which a beam to be accelerated passes one of the projections is increased as beam energy is increased and then decreased; and
in a magnetic pole outer circumferential region of the recess, an inlet of an extraction channel from which a beam accelerated to a predetermined energy is extracted to outside the particle beam accelerator is provided.

7. A particle beam accelerator comprising:
an acceleration cavity that enables modulation of a frequency of radiofrequency electric field to accelerate a beam; and a magnetic device that produces a static magnetic field, wherein: the magnetic device has a return yoke and a pair of magnetic poles fixed to the return yoke;

the pair of magnetic poles are placed at positions in surface symmetry with respect to a middle plane in a space sandwiched between the pair of magnetic poles;

on a face opposite to the middle plane of the magnetic pole, a recess and a projection are alternately placed along a beam circling direction;

in the projection, an angle between a tangent of a boundary between the projection and the recess and a tangent of a boundary between the projection and the recess on an opposite side of the projection and the recess is decreased as beam energy is increased and then increased; and in a magnetic pole outer circumferential region of the recess, an inlet of an extraction channel from which a beam accelerated to a predetermined energy is extracted to outside the particle beam accelerator is provided.

* * * * *